United States Patent [19]

Palmaer et al.

[11] Patent Number: 4,830,138

[45] Date of Patent: May 16, 1989

[54] PRESSURE RING FOR EAR COVER

[75] Inventors: Tore Palmaer, Gnosjo; Leif Palmaer, Varnamo, both of Sweden

[73] Assignee: Finnveden Holding AB, Sweden

[21] Appl. No.: 165,615

[22] Filed: Mar. 8, 1988

[51] Int. Cl.$^4$ ............................................. H04R 25/00
[52] U.S. Cl. ....................................... 181/129; 2/209; 381/158; 381/183
[58] Field of Search ................ 181/126, 129; 381/158, 381/183, 187–189; 2/209, 423

[56] References Cited

U.S. PATENT DOCUMENTS

| | | | |
|---|---|---|---|
| 3,805,298 | 4/1974 | Aho | 2/209 |
| 3,944,018 | 3/1976 | Satory | 181/129 X |
| 4,572,323 | 2/1986 | Randall | 181/129 |
| 4,572,324 | 2/1986 | Fidi et al. | 181/129 |

FOREIGN PATENT DOCUMENTS

| | | |
|---|---|---|
| 1925495 | 11/1969 | Fed. Rep. of Germany . |
| 1954039 | 7/1970 | Fed. Rep. of Germany . |
| 2103305 | 8/1974 | Fed. Rep. of Germany . |

Primary Examiner—B. R. Fuller
Attorney, Agent, or Firm—Ostrolenk, Faber, Gerb & Soffen

[57] ABSTRACT

A pressure ring for an earmuff, an earphone, or the like, wherein the earmuff, or the like, includes a sealing ring which is applied against the head of the wearer around the ears and the pressure ring is behind and applies pressure to the sealing ring at the top, contact surface of the pressure ring. The contact surface is taller above the base surface of the pressure ring at the peripheral outer edge of the pressure ring than at the peripheral inner edge of the pressure ring so that the sealing ring is concave and the surface of the ear cover over the ear is concave. At least the peripheral outer edge of the contact surface varies in height between the taller upper and lower ends of the pressure ring, on the one hand, and the central region of the pressure ring, on the other hand. At least one groove channel wraps at least partially around the pressure ring and extends into the pressure ring from the contact surface. Barriers in the channel block the channel from extending completely around the pressure ring. Openings communicate between adjacent concentric grooves of the channel. The barriers and openings are placed to define short-length sound traps in the channel.

20 Claims, 2 Drawing Sheets

PRESSURE RING FOR EAR COVER

BACKGROUND OF THE INVENTION

The present invention relates to a pressure ring for an ear cover, like an earmuff, earphones, or the like product, which is designed to include a sealing ring.

Known earmuffs, earphones, or the like, include an ear covering cup that is provided with a sealing ring to provide right contact against the head in the region of the wearer's ear. The sealing ring is supported by a flat pressure ring behind the sealing ring. The pressure ring is in the form of a separate ring or is an integrated part of the ear covering cup. Pressure is applied on the earmuff by a headband, so that the sealing ring and the pressure ring behind it are elastically deformed into contacting the wearer's head. It has been found that the contact pressure has caused certain persons discomfort when they wear the above described earmuffs for long periods of time. It has also proven difficult to obtain sufficiently tight contact against the head. One solution to these problems has been to increase the thickness of the sealing ring. But this has resulted in a deteriorated dampening effect.

SUMMARY OF THE INVENTION

The object of the present invention is to eliminate the above drawbacks of known ear covers, like earmuffs, or the like, and to provide a pressure ring of the type described in the introduction which satisfactorily fits against the head without causing discomfort or deteriorating the properties of the earmuff.

According to the invention, a pressure ring has an arched, concave contact surface to effect substantially tight contact against the head in the region around the wearer's ear. The contact surface has an inner peripheral edge and an outer peripheral edge which are located at different heights above the base surface of the pressure ring creating the concavity.

The height of at least the outer peripheral edge and also perhaps of the inner peripheral edge above the base surface are suitably higher at the upper and lower ends of the pressure ring than in the central region of the pressure ring between those ends.

According to the invention, the pressure ring may also be provided with a channel extending into the pressure ring from the inside or sealing ring facing side toward the outside of the pressure ring. This channel runs along a substantial portion of the circumference of the pressure ring. The channel suitably runs once or several times around the pressure ring. The channel is designed to produce one or more sound traps.

According to a preferred embodiment, the channel may be comprised of a number of concentric grooves located between the contact surface and base surface of the sealing ring. Each of the grooves is provided with a barrier blocking the groove from extending around the entire circumference of the pressure ring and an opening connecting that groove to adjacent grooves. The barrier and opening are arranged so as to make the channel as long as possible.

Other objects and features of the invention are described with reference to the accompanying drawings.

DESCRIPTION OF THE PREFERRED EMBODIMENTS

Figure 1:
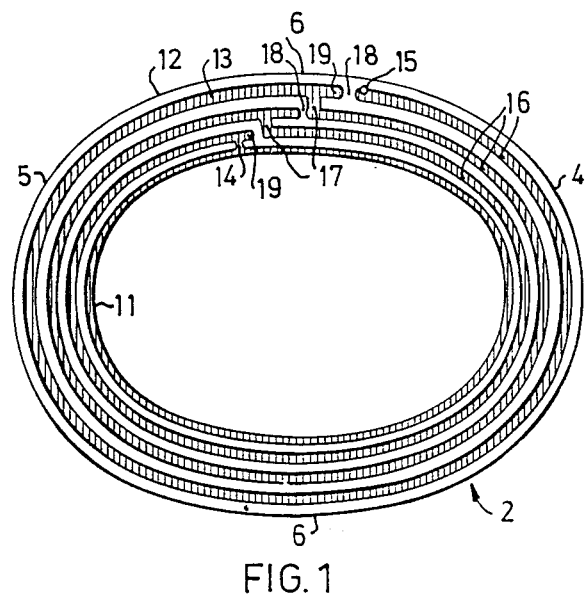
FIG. 1 is a plan view of a pressure ring according to the invention.

The Figures show two embodiments of a pressure ring for an ear cover. For each embodiment, a pressure ring 2 and a sealing ring 3 (shown in FIG. 3) designed for an earmuff 1 (also shown in FIG. 3) are shown. The pressure ring 2 is suitably oval in shape, comprising an upper end 4 to the right in FIG. 1, a lower end 5 to the left and a central region 6 between them. The annular pressure ring 2 is provided with a base surface 7 at its outside or bottom in FIG. 2, a contact surface 8 at its inside or top and an outer surface 9 beneath the base. The outer surface 9 is provided with attachment means 10 for attaching the base to the earmuff, cup, or the like.

The annular pressure ring 2 also comprises a radially inner or peripheral edge 11 at its contact surface and a radially outer or peripheral edge 12 also at its contact surface.

A channel 13 extends from the radial inside of the pressure ring at an opening 14 to its radial outside at a hole 15. The channel 13 may comprise concentric grooves 16 communicating with each other via radially extending, narrow width openings 17. Each groove 16 is limited by a barrier 18 which prevents each groove from closing upon itself. The channel 13 may also be provided with a number of short circumferential length sound traps 19, where a groove 16 projects past a respective radial opening 17 into that groove.

The pressure ring 2, according to the invention, may be made as a homogenous unchanneled unit, but is preferably provided with the channel 13. From a manufacturing point of view, this is very suitable and also reduces the weight of the pressure ring, as compared with a homogeneous one. The pressure ring 2 may thus suitably be produced from a plastic material by means of injection molding. However, other materials and fabrication methods are of course feasible.

Figure 2:
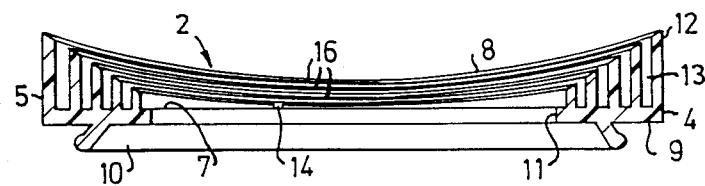
FIG. 2 shows a cross-section through the pressure ring in FIG. 1.

An additional advantage of the channel 13 is that pressure is equalized between the inside and outside of the earmuff. Known earmuffs are provided with a small hole in their cup to achieve pressure equalization. But, some sound has been found to penetrate through the hole, deteriorating the protective qualities of the earmuff. In the present invention, penetration of sound is limited by the channel 13 being made as long as possible. This is achieved by the channel 13 running along a substantial portion of the circumference of the pressure ring 2, and preferably around once or possibly even several times as shown in FIG. 2. The channel may be in the form of a spiral or zig-zag pattern. However, the embodiment shown in FIG. 1 has proven advantageous from the manufacturing point of view and has also enabled one or more sound traps 19 to be included.

The proposed channel may thus be designed with concentric grooves 16, each having a height dimension in the direction between the contact surface 8 and the base surface 7 of the sealing ring. Each of the grooves 16 is provided with its own barrier 18 which blocks the groove 16 and prevents it making a full circuit around the pressure ring. A radially directed opening 17 joins the groove 16 to adjacent grooves. The barrier 18 and opening 17 are thus substantially arranged to make the channel 13 as long as possible. In the embodiment shown, the barrier 18 and opening 17 have been spaced from each other in order to form a sound trap 19 at the end of each groove 16 for further inhibiting spreading of the sound.

A number of measurements have been performed on several people to determine the dimensions of the pressure ring 2 so that the contact surface 8 will fit as tightly against the head as possible. It has been found that the topography of the head is most uniform closest to the ear, has recesses at the temple and behind the jaw which are located diagonally opposite each other, and is raised close to the ear, and is more prominent in women than in men. Based on these measurements, it is possible to adjust the pressure ring to fit the left or right ear, the upper or lower side and also to fit for men or women. The shape of the ring can be adjusted to the topography of the region around the ear, thus reducing the contact pressure without the earmuff falling off or giving increased dampening effect, especially by allowing the use of a thinner ring.

According to the invention, the inner edge 11 and outer edge 12 at the contact surface 8 are located at different levels or heights above the base surface 7 of the pressure ring. Although it is advisable to shape the pressure ring 2 to fit the right or left ear, from a practical point of view it may be advantageous to shape the pressure rings 2 symmetrically. To this end, the levels or heights of the inner edge 11 and of the outer edge 12 above the base surface 7 are located higher at the upper and lower ends 4, 5 than at the central region 6 of the pressure ring. This height difference in edge 12 can be seen in FIG. 2. The accompanying table illustrates it also. The average height difference between the level of the inner edge 11 and the level of the outer edge is 2.5±0.9 mm. As a result, the pressure ring is arched or concave, giving the sealing ring above it a concave inside surface and making the surface of the ear cover against the head concave.

To obtain the required information for shaping the pressure ring around the entire ear cover, a number of measurements were taken around the ear at a distance corresponding to the limit of the inner edge and also at a distance corresponding to the limit of the outer edge. Ten measurements were performed around each ear and the results are shown in the following table where U denotes the top of the ear; N denotes the bottom of the ear; A-D denote points measured evenly around each side of the ear; i denotes the inner measurement path; and y denotes the outer measurement path.

Figure 3:
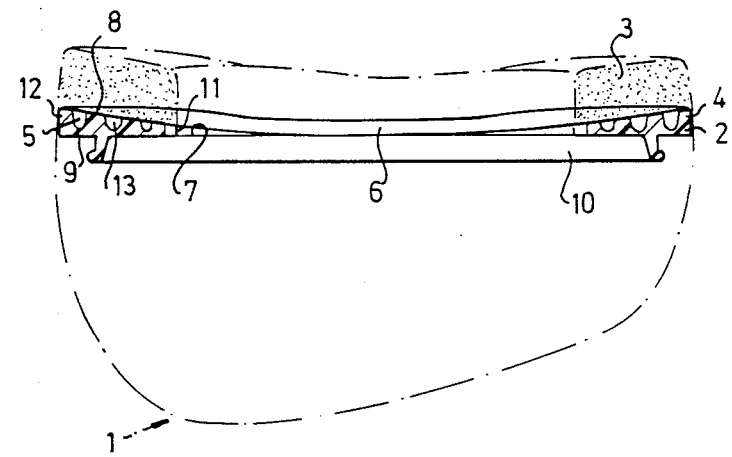
FIG. 3 shows a cross-section through an alternative embodiment of the pressure ring according to the invention, also shown here schematically fitted into an earmuff.

The sealing ring 3 for any embodiment is shown in FIG. 3. It may be of foam plastic covered with a non-porous protective layer. The protective layer may also extend along the inside of the foam plastic ring in order to increase the dampening function of the channels. The pressure ring in FIG. 3 is of shorter height at its outer edge than that of FIG. 2.

Of course, the invention can be modified with respect to the fit if, for instance, measurements in other countries give different average values. Certain adjustments may also be required for extra equipment such as audio headphones, walkie-talkies, etc.

Although the present invention has been described in connection with a plurality of preferred embodiments thereof, many other variations and modifications will now become apparent to those skilled in the art. It is preferred, therefore, that the present invention be limited not by the specific disclosure herein, but only by the appended claims.

| L-ear = R-ear | | WOMEN L & R | | MEN L & R | | WOM + MEN L & R | | WOM + MEN INTER-CHANGEABLE | | REDUCED −1.5 m | |
|---|---|---|---|---|---|---|---|---|---|---|---|
| Measured point i | | | | | | | | | | | |
| U | U | 1.1 | | 0.8 | | 0.9 | | 2.3 | | 1 | |
| A A1 | A1 A | 1.1 | 2.4 | 0.7 | 2.6 | 0.8 | 2.5 | 1.4 | 3 | 0.1 | 1.7 |
| B B1 | B1 B | 1.7 | 2.3 | 1.3 | 2.6 | 1.5 | 2.5 | 1.3 | 2.2 | 0 | 0.9 |
| C C1 | C1 C | 2.5 | 1 | 1.4 | 1 | 1.9 | 1 | 2.2 | 1.3 | 0.9 | 0 |
| D D1 | D1 D | 4.3 | 2.1 | 2.6 | 2 | 3.4 | 2 | 3 | 1.4 | 1.7 | 0.1 |
| N | N | 4 | | 3.9 | | 4 | | 2.3 | | 1 | |
| MEASURED POINT y | | | | | | | | | | | |
| U$_{rear}$ | U$_{rear}$ | 4 | | 2.4 | | 3.2 | | 4 | | 2.7 | |
| A A1 | A1 A | 3.2 | 4.6 | 2.4 | 4.9 | 2.8 | 4.6 | 2.9 | 5.8 | 7.6 | 4.5 |
| B B1 | B1 B | 4.1 | 3.6 | 3.1 | 4.3 | 3.6 | 4 | 2.8 | 4.9 | 1.5 | 3.6 |
| C C1 | C1 C | 6.5 | 2.2 | 5.2 | 2 | 5.8 | 2 | 4.9 | 2.8 | 3.6 | 1.5 |
| D D1 | D1 D | 8.3 | 2.9 | 5.7 | 3 | 6.9 | 2.9 | 5.8 | 2.9 | 4.5 | 1.6 |
| N | N | 4.5 | | 4.9 | | 4.7 | | 4 | | 2.7 | |
| MEASURED POINT y − i | | | | | | | | | | | |
| U | U | 2.9 | | 1.7 | | 2.3 | | 1.7 | | | |
| A A1 | A1 A | 2.4 | 2.5 | 1.7 | 2.7 | 2.1 | 2.8 | 1.5 | 3.2 | | |
| B B1 | B1 B | 2.2 | 1.7 | 2 | 1.8 | 2.1 | 1.6 | 1.6 | 2.9 | | |
| C C1 | C1 C | 4.3 | 1.2 | 3.9 | 0.8 | 4.1 | 1 | 2.9 | 1.6 | | |
| D D1 | D1 D | 4.3 | 0.7 | 3 | 1.2 | 3.6 | 0.9 | 3.2 | 1.5 | | |
| N | N | 0.8 | | 1.2 | | 1 | | 1.7 | | 7.2 | |
| MEASURED POINT $\frac{i+y}{2}$ | | | | | | | | | | | |
| U | U | 2.3 | | 1.9 | | 2.1 | | 3 | | | |
| A A1 | A1 A | 1.5 | 4 | 2.3 | 3 | 1.9 | 3.5 | 2.2 | 4.5 | | |
| B B1 | B1 B | 2.4 | 2.6 | 2.7 | 3.4 | 2.5 | 3 | 2 | 3.5 | | |
| C C1 | C1 C | 3.9 | 2 | 4.1 | 0.8 | 4 | 1.4 | 3.5 | 2 | | |
| D D1 | D1 D | 5.2 | 3 | 5 | 1.9 | 5.1 | 2.5 | 4.3 | 2.2 | | |

-continued

| L-ear = R-ear | | WOMEN L & R | MEN L & R | WOM + MEN L & R | WOM + MEN INTER-CHANGEABLE | REDUCED −1.5 m |
|---|---|---|---|---|---|---|
| N | N | 4.1 | 3.7 | 3.9 | 3 | |

What is claimed:

1. A pressure ring for an ear cover, earmuff, or the like, wherein the ear cover includes a sealing ring to be applied against a wearer's head around the ear, the pressure ring being disposed behind and outside the sealing ring;

the pressure ring having a base surface on a side thereof outward of the sealing ring; the pressure ring including an arched contact surface for disposal behind the sealing ring, the contact surface being shaped for effecting substantially tight contact against the wearer's head around the ear, the pressure ring having an outer edge toward an outer periphery thereof and an inner edge defining an inner periphery of the ring, the contact surface of the pressure ring having different height levels above the base surface of the pressure ring between the inner edge and the outer edge of the pressure ring.

2. The pressure ring of claim 1, wherein the contact surface at the outer edge is generally at a greater height above the base surface of the contact surface at the pressure ring than at the inner edge.

3. The pressure ring of claim 2, wherein the height above the base of the contact surface at least at the outer edge surface of the pressure ring is variable around the pressure ring.

4. The pressure ring of claim 3, wherein the pressure ring has opposite upper and lower ends and has a central region between the opposite ends, and the height above the base surface of the contact surface is greater at the upper and lower ends of the pressure ring than at the central region of the pressure ring.

5. The pressure ring of claim 4, wherein the height of the contact surface above the base surface at the inner edge of the contact surface is higher at the upper and lower ends than at the central region of the pressure ring.

6. The pressure ring of claim 3, wherein the height above the base surface of the contact surface at the outer edge is greater than the height above the base surface of the contact surface at the inner edge by an average of 2.5±0.9 mm.

7. The pressure ring of claim 1, wherein between the outer edge and the inner edge of the pressure ring, at least one channel extends from inside of the pressure ring facing the sealing ring toward an outside of the pressure ring at the base surface and extends along at least a substantial portion of a circumferential length of the pressure ring.

8. The pressure ring of claim 7, wherein the channel further includes at least one sound trap defined in the channel.

9. The pressure ring of claim 7, wherein the channel is of such length around the pressure ring and is so shaped as to extend at least once at least almost entirely around the pressure ring.

10. The pressure ring of claim 9, wherein the channel is of such length around the pressure ring and is so shaped as to extend around the pressure ring a plurality of times, with each successive passage of the channel around the ring spaced further from the inner edge and closer to the outer edge.

11. The pressure ring of claim 10, wherein the channel further includes at least one sound trap defined in the channel.

12. The pressure ring of claim 10, wherein the channel is comprised of a plurality of concentric grooves defined in the pressure ring extending into the pressure ring in a direction outward from the contact surface toward the base surface of the pressure ring.

13. The pressure ring of claim 12, wherein the pressure ring includes barriers along the length of at least some of the grooves of the channel for blocking that channel from extending completely around the pressure ring.

14. The pressure ring of claim 13, further comprising openings extending between adjacent grooves and connecting the grooves for elongating the channel which is comprised of a plurality of the grooves.

15. The pressure ring of claim 14, wherein the openings connecting adjacent grooves are near to but spaced around the ring a short distance from at least some of the barriers for defining sound traps in a groove between the opening to a groove and the barrier near to that opening.

16. The pressure ring of claim 12, further comprising openings extending between adjacent grooves and connecting the grooves for elongating the channel which is comprised of a plurality of the grooves.

17. The pressure ring of claim 10, wherein the contact surface at the outer edge is generally at a greater height above the base surface of the contact surface at the pressure ring than at the inner edge; the height above the base surface of the contact surface at least at the outer edge surface of the pressure ring is variable around the pressure ring.

18. The pressure ring of claim 17, wherein the pressure ring has opposite upper and lower ends and has a central region between the opposite ends, and the height above the base surface of the contact surface is greater at the upper and lower ends of the pressure ring than at the central region of the pressure ring.

19. A pressure ring for an ear cover, earmuff, or the like, wherein the ear cover includes a sealing ring to be applied against a wearer's head around the ear, the pressure ring being disposed behind and outside the sealing ring;

the pressure ring having a base surface on a side thereof outward of the sealing ring; the pressure ring including an arched contact surface for disposal behind the sealing ring, the contact surface being shaped for effecting substantially tight contact against the wearer's head around the ear, the pressure ring having an outer edge toward an outer periphery thereof and an inner edge defining an inner periphery of the ring, between the outer edge and the inner edge of the pressure ring, at least one channel extends from inside of the pressure ring facing the sealing ring toward an outside of the pressure ring at the base surface and extends along at least a substantial portion of the circumferential length of the pressure ring.

20. The pressure ring of claim 19, wherein the channel is of such length around the pressure ring and is so shaped as to extend around the pressure ring a plurality of times, with each successive passage of the channel around the ring being spaced further from the inner edge and closer to the outer edge.

* * * * *